US006620793B2

(12) United States Patent
Toffano et al.

(10) Patent No.: US 6,620,793 B2
(45) Date of Patent: Sep. 16, 2003

(54) THERAPEUTIC USE OF GANGLIOSIDE $GM_1$ IN THE TREATMENT OF SPINAL CORD INJURY

(75) Inventors: Gino Toffano, Padua (IT); Alberta Leon, Padua (IT); Marino Massarotti, Padua (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 0 days.

(21) Appl. No.: 10/125,810

(22) Filed: Apr. 18, 2002

(65) Prior Publication Data

US 2003/0153517 A1 Aug. 14, 2003

Related U.S. Application Data

(63) Continuation of application No. 09/564,384, filed on Apr. 27, 2000, now abandoned, which is a continuation of application No. 08/957,784, filed on Oct. 24, 1997, now abandoned, which is a continuation of application No. 08/443,761, filed on May 18, 1995, now abandoned, which is a continuation of application No. 07/821,059, filed on Jan. 16, 1992, now abandoned.

(30) Foreign Application Priority Data

Dec. 23, 1991 (IT) .......................................... PD91A0234

(51) Int. Cl.$^7$ ............................................ A61K 31/715
(52) U.S. Cl. .............................. 514/25; 514/54; 514/62; 514/169; 514/171
(58) Field of Search .............................. 514/25, 54, 62, 514/169, 171

(56) References Cited

U.S. PATENT DOCUMENTS

| | | | |
|---|---|---|---|
| 4,849,413 A | 7/1989 | della Valle et al. | ............ 514/54 |
| 4,851,521 A | 7/1989 | della Valle et al. | ........ 536/55.1 |
| 4,940,694 A | 7/1990 | della Valle et al. | ............ 514/25 |
| 5,068,224 A | 11/1991 | Fryklund et al. | ............. 514/21 |

OTHER PUBLICATIONS

Geisler, F.H. et al., New England Journal of Medicine, 324, No. 26, pp. 1829–1838 (Jun. 1991).
Walker, M.D., New England Journal of Medicine, 324, No. 26, pp. 1885–1887 (1991).
Sabel, B.A., Pharmacological Approaches to the Treatment of Brain and Spinal Cord Injury, ed. D.G. Stein and B.A. Sabel, Chapter 9, pp. 167–194 (1988).
Janssen et al., SPINE, vol. 14, No. 1, pp. 23–32 (1989).
Hadjiconstantinou, M. et al., Brain Research, vol. 366, pp. 343–345 (1986).
Geisler, F.H. et al., Acta Neurobiol. Exp., vol. 50, pp. 515–521 (1990).
Young, W., Neural Regeneration and Transplantation, pp. 157–169 (1989).

Beattie, M.S. et al., Pharmacological Approaches to the Treatment of Brain and Spinal Cord Injury, ed. D.G. Stein and B.A. Sabel, Chapter 3, pp. 43–73 (1988).
Leon, A. et al., Supplement III, Stroke, vol. 21, No. 11, pp. 95–97 (1990).
Carolei, A. et al., Cerebrovascular and Brain Metabolism Reviews, vol. 3, pp. 134–157 (1991).
Geisler, F.H. et al., Ricerche Sperimentali, pp. 167–172, in "I tumori primitivi del midollo spinale". C.A. Pagani et al, eds., Torino, Minerva Medica 1991.
Geisler et al., abstracts from the AANS and CNS, and the Symposium of the XXXI Int. Congress of Physiol. Sci., Cancun, Mexico—Feb. 12, 1989; Warsaw, Poland—Jul. 4–7, 1989; Rome, Italy—Feb. 20–23, 1991.
Hall et al., Chemical Abstracts 101:84196h (1984); 105:91569t (1986).
Braughler et al., Chemical Abstracts 101:123343a (1984).
Bose et al., Chemical Abstracts 104:102429e (1986).
Fusco et al., Chemical Abstracts 105:131574z (1986).
Braughler et al., Chemical Abstracts 107:90251n (1987).
Gorio et al., Chemical Abstracts 107:147151m (1987).
Fusco et al., Chemical Abstracts 110:1528e (1989).
Holtz et al., Chemical Abstracts 115:22443s (1991).
Young, W., Neurology Neurosurgery & Psychiatry, vol. 55, pp. 635–639 (1992).
Fishman et al., Science, 194, pp. 906–915 (1976).
Willinger et al., Dev. Biol., 74, pp. 101–117 (1980).
Obata et al., Integrative Control Functions of the Brain, Ed. Ito et al., 2, pp. 5–14 (1979).
Gorio et al., Brain Research, 197, pp. 236–241 (1980).
Syennerholm, J. Neurochem. 10, pp. 613–623 (1963).
Tettamanti et al., Biochimica et Biophysica Acta, 296, pp. 160–170 (1973).
Purpura et al., Brain Research, 143, pp. 13–26 (1977).
Commissiong et al., Brain Research, 380, pp. 205–215 (1986).
Sabel et al., Nature, 323, p. 493 (1986).
Braughler et al., J. Neurosurg. 61:290–295 (1984).
Bose et al., Neuroscience Letters 63:165–169 (1986).
Hall et al., Exp. Brain Res. (Suppl. 13):63–73 (1986).
Braughler et al., J. Neurosurg. 67:102–105 (1987).
Bracken et al., New Engl. J. Med., 322 (20):1405–1411 (May 17, 1990).
Hall, Neurosteroids & Brain Function, Fidia Res. Series, vol. 8, pp. 55–60, (1991).

*Primary Examiner*—Kathleen K. Fonda
(74) *Attorney, Agent, or Firm*—Leonard R. Svensson; Birch, Stewart, Kolasch & Birch, LLP

(57) ABSTRACT

The invention relates to a method for amelioration of neurological outcome in humans with spinal cord damage by administration of ganglioside $GM_1$. Another object of the present invention is to provide combination therapies for the treatment of spinal cord damage comprised of the administration of the ganglioside $GM_1$ and other drugs which have therapeutical benefit in patients with spinal cord damage, preferably methylprednisolone.

6 Claims, 1 Drawing Sheet

THERAPEUTIC USE OF GANGLIOSIDE $GM_1$ IN THE TREATMENT OF SPINAL CORD INJURY

This application is a continuation of application Ser. No. 09/564,384, filed on Apr. 27, 2000, now abandoned, which is a continuation of Application Ser. No. 08/957,784, filed on Oct. 24, 1997, now abandoned, which is a continuation of application Ser. No. 08/443,761 filed on May 18, 1995, now abandoned, which is a continuation of application Ser. No. 07/821,059 filed on Jan. 16, 1992, now abandoned, the entire contents of which are hereby incorporated by reference.

BACKGROUND AND FIELD OF THE INVENTION

Spinal cord injury is a devastating injury with, today, no significantly useful therapy. Emergency medical treatment for spinal-cord injury patients has included prompt triage and intensive rehabilitation. These therapies have somewhat increased or optimized remaining neurologic functions in those patients and prevented further injury to the spinal cord. However, only a minority of patients ever achieve any major neurologic recovery. As a result, no effective acute treatment or rehabilitation therapy is presently available for the approximately 10,000 patients per year which suffer from major spinal cord injury and the consequent permanent disability.

Development of effective treatments is also made more difficult because it is difficult to extrapolate to therapy in humans from animal studies. There is significant controversy about whether any and which animal models best simulate spinal cord injuries in humans, about whether the models are reproducible, and therefore whether studies in animals provide useful information for possible human therapy. It is, therefore, one object of the present invention to provide a method for neurological recovery in humans with spinal cord injury by administration of the ganglioside $GM_1$.

It is another object of the present invention to provide a combination therapy for the treatment of spinal cord injury comprised of administration of the ganglioside $GM_1$ and preferably methylprednisolone.

DETAILED DESCRIPTION OF THE INVENTION

Figure 1:
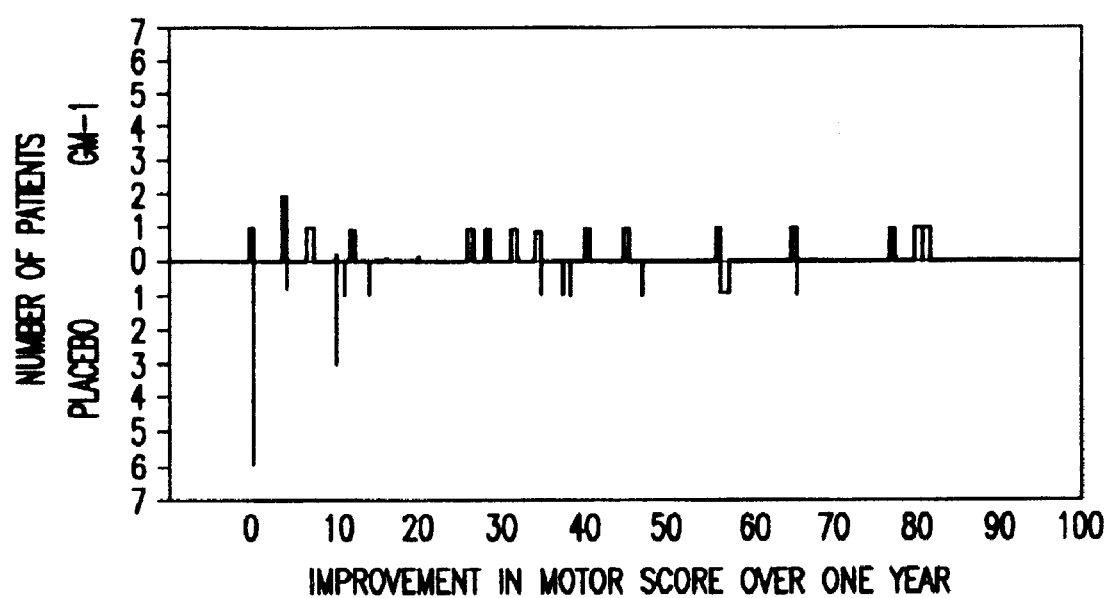
FIG. 1 shows the distribution of improvement in ASIA motor scores from study entry to the end of the one-year follow-up.

Gangliosides are complex glycolipid molecules which are natural components of cellular membranes and have a structure containing a carbohydrate portion to which is linked a ceramide and sialic acid moiety. The carbohydrate portion includes at least one galactose or glucose moiety and at least one N-acetylglucosamine or N-acetylgalactosamine moiety. The general structure of a ganglioside can then be represented by the following formula:

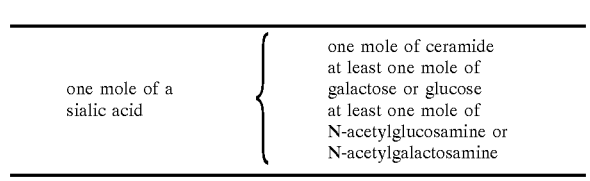

where all of the moieties are linked by a glycosidic bond.

Numerous gangliosides have been identified and have been found to be particularly abundant in nerve tissue, especially in brain tissue. Various studies have shown that the most important of the sialic acids found in gangliosides are N-acetyl-neuraminic acid (NANA) and, to a lesser degree, N-glycolylneuraminic acid. Of the numerous gangliosides which have been identified, the following gangliosides, labeled by their international symbols, have been found to exist in significant amounts in ganglioside mixtures extracted from bovine brain tissue:

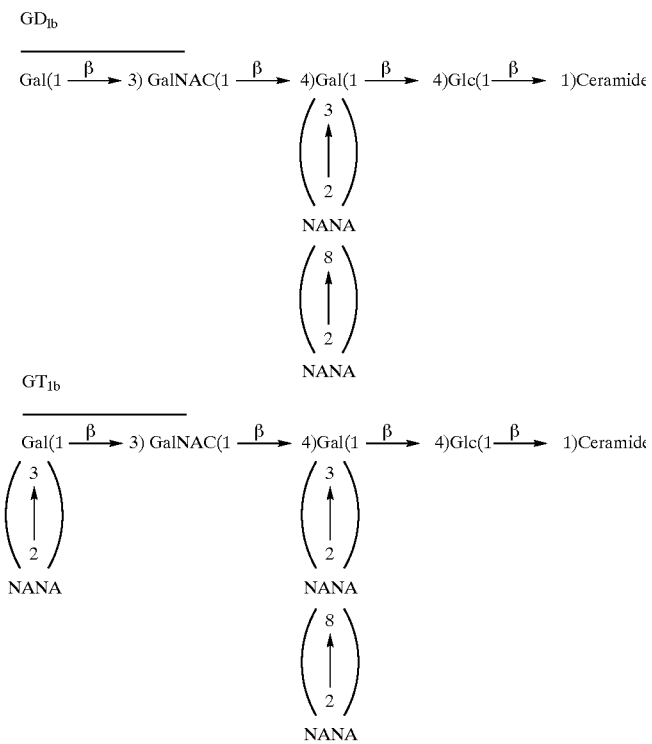

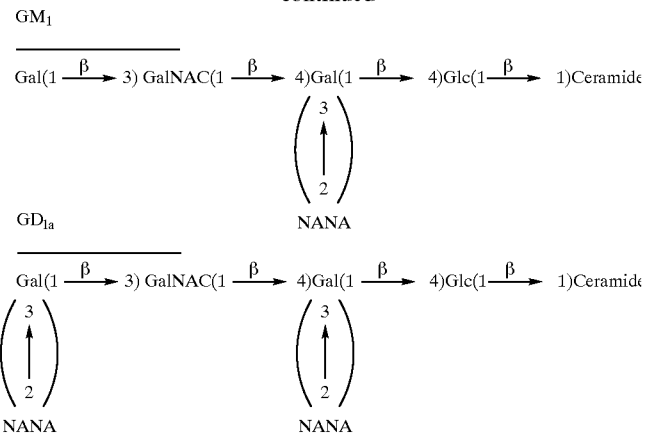

where Glc represents glucose, GalNAC represents N-acetylgalactosamine, Gal represents galactose, NANA represents N-acetyl-neuraminic acid.

Since gangliosides are mainly associated with neuronal membranes, it has been suggested that they may play a role in the transfer of information across these membranes (Fishmann, P. H., Brady, R. O. (1976): Science, 194, 906–915). Such a role is now envisaged in the recognition and interaction phenomena that underlie the differentiation, maturation and synaptic contacting of neuronal circuitry. In particular one ganglioside, $GM_1$ (monsialoganglioside), has been implicated in neuronal differentiation processes in mouse cerebellum (Willinger, M., Schachner, M. (1980). Dev. Biol., 74, 101–107) and in neurite induction in cortical neurons in cats (Purpura, D. P., Baker, H. J. (1977), Brain Res. 143, 13–26).

A specific role for ganglioside $GM_1$ in facilitating the formation of synaptic contacts was suggested by experiments which found that $GM_1$,-enrichment would facilitate the formation of neuromuscular junctions in nerve-muscle cocultures (Obata, K. and Handa, S. (1979). In "Integrative Control Functions of the Brain", Ed. Ito et al., 2, 5–14). A distinct pharmacological effect of the administration of exogenous gangliosides (a bovine brain extraction product) was defined by Gorio et al., (Gorio, A., Carmignoto, G., Facci, L., Finesso, M. (1980), Brain Res., 197, 236–241) as a reinnervation-stimulating activity due to enhanced nerve sprouting, resulting in early functional recovery after traumatic peripheral nerve damage. This pharmacological action was found to be operative also in the central nervous system (CNS).

In fact, the mammalian CNS is now known to be able to express self-repair by morphofunctional adaptive responses to environmental perturbations (i.e. neuroplasticity). This phenomenon occurs not only during development but also after injury to the adult nervous system. Neurons can modify their metabolism, excitability, and gene expression in an attempt to restore function.

The degree of neuroplastic response after CNS injury may bear an inverse relation to the degree of neuronal damage. This expression of neuroplasticity is probably regulated by specific neuronotrophic factors present in the CNS throughout the life of the organism. Neuronotrophic factors are the protein molecules on which a neuron depends for its correct development and function in adulthood. The classic example is nerve growth factor, although other factors have been identified. Pharmacologic strategies aimed at both reducing the acute evolution of neuronal damage and increasing the long-term efficacy of neuronotrophic factors offer the possibility of functional neurologic recovery.

Numerous studies have demonstrated that $GM_1$ can decrease neuronal cell death and potentiate the neuronotrophic effects of nerve growth factor in neuronal cell cultures. The proneuronotrophic effect of $GM_1$ is not limited to nerve growth factor; it also affects other defined trophic molecules and diverse neuronal types. Complementary in vivo experiments have shown that the ganglioside may potentiate the effects of nerve growth factor administered intraventricularly after lesions to forebrain cholinergic neuronal systems (see Skaper et al. for a recent review). Furthermore, $GM_1$ alone has been reported to decrease neuronal cell loss and facilitate recovery-after a variety of acute CNS insults. These results suggest that systemically administered $GM_1$ may be useful in facilitation of the expression of separative responses necessary for amelioration of neurological outcome.

The present study focused on the effective treatment with the ganglioside $GM_1$, which is one of the major gangliosides present in mammalian nerve tissue. The term ganglioside is an accepted trivial group name for sialic acid-containing glycosphingolipids. These complex glycolipids are acidic, water-soluble and not dialyzable. The ganglioside molecule is amphipathic, consisting of a lipophilic moiety (ceramide) made of sphingosine and fatty acids, in particular stearic acid, and a hydrophilic oligosaccharide moiety. Ganglioside $GM_1$ is a monosialoganglioside (the ganglioside family is differentiated by the varying number and position of sialic acid residues present in the molecule). Monosialioganglioside $GM_1$ may be considered a basic compound in the ganglioside series, since metabolic manipulation of more complex gangliosides will invariably lead to ganglioside $GM_1$. Svennerholm (Svennerholm, L. (1963), J. Neurochem., 19, 613–623) proposed a classification system and nomenclature, which has entered into common use. Other denominations are:

Monosialotetrahexosylganglioside, sodium salt $II^3$I-alpha-N-acetylneuraminosyl-gangliotetraglycosyl ceramide, sodium salt (IUPAC-IUB name)

$II^3$-alpha-NeuAc-GgOse,Cer, sodium salt (IUPAXI-UB abbreviation)

Chemical Abstract Registry Number: RN (37758-47-7)

The symbol $GM_1$ conforms to the Svennerholm system. More complex abbreviatory names were devised by the IUPAC-IUB Lipid Document (1977).

Extraction and Purification Procedures

The monosialoganglioside is a biological substance obtained from bovine brain with the following structural formula:

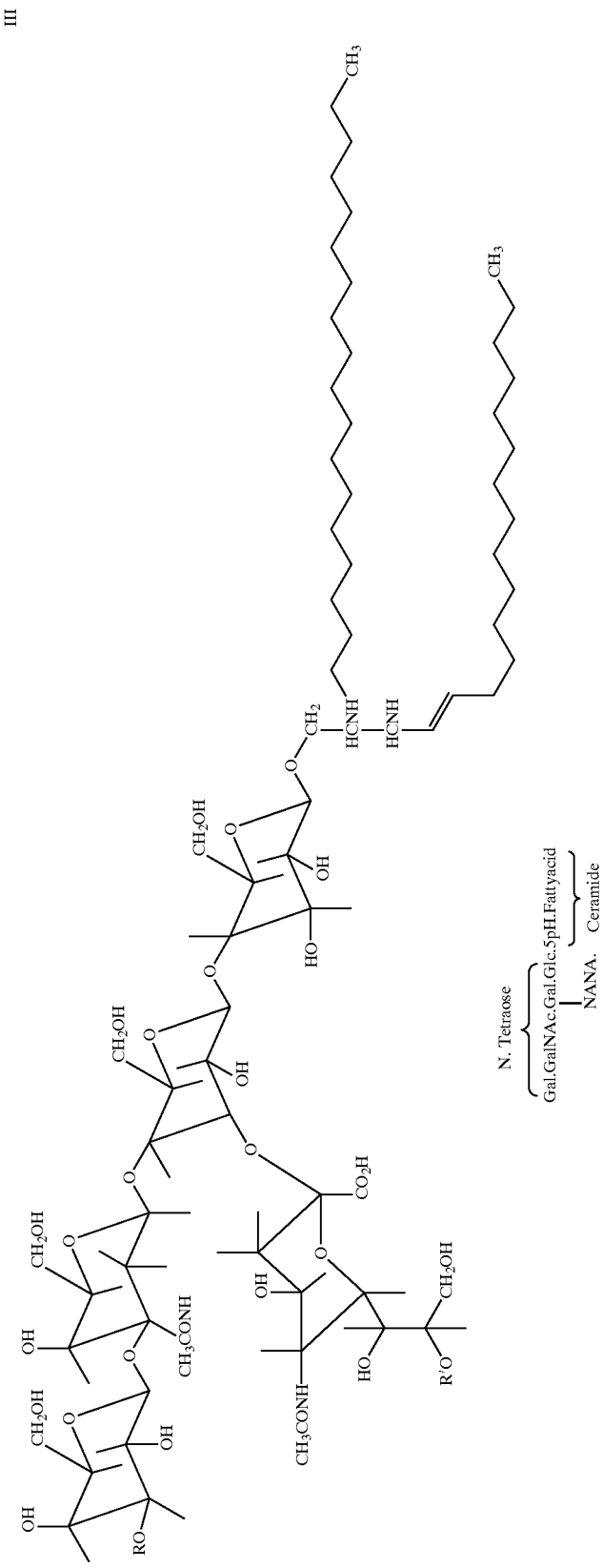

The sodium salt of monosialotetrahexosylganlioside $GM_1$ can be isolated as a highly purified product according to procedures known in the art, such as the procedure described by Tettarnanti et al. (Biochimica et Biophysica Acta, 296 (1973) 160–170) or obtained from Fidia S.p.A., Abano Terme, Italy.

As one exemplary preparation procedure, starting from frozen cattle brains, a multi-step separation procedure, based on solvent extraction, liquid/liquid partitioning, phospholipid removal by methanolysis, and molecular filtration yields a highly purified ganglioside mixture (itself used as active ingredient in injectable preparations), which contains ganglioside $GM_1$ in a percentage between about 18 and 24% in comparison to a reference working standard with known structure and purity. This compound is separated from the mixture by a, two-step High Performance Liquid Chromatography procedure, giving a final yield of approximately 75% of the theoretical value. The obtained substance is converted to the sodium salt, dialyzed and precipitated. The precipitate is redissolved in water, submitted to sterilizing filtration and lyophilized. The purity of the compound obtained is more than 98% referring to dry weight by photodensitometry and HPLC assay in comparison to a reference working standard with known structure and purity.

The compound obtained after this purification has the following chemical characteristics and specifications:

Molecular Weight 1.569 (Calculated on the basis of the presence of 1 mole of NANA, 1 mole of glucose, 2 moles of galactose, 1 mole of galactosamine, sphingosine 18:1, stearic acid and sodium salt).

Appearance

Odourless, hygroscopic, white-cream powder.

Solubility

Soluble in water, methanol-water and methanol-chloroform. Virtually insoluble in methanol, acetone, chloroform, ether and hexane.

Melting Point 207–230° C.

Specifications

| | |
|---|---|
| Identity | positive in three tests (structural analysis by gas chromatography for the singular components, I.R. spectrum, TLC in 2 different solvents, identity of sodium) |
| pH (1% w/v) | 7.0–8.5 |
| Loss on drying | less than 3.01 |
| Impurities (TLC) | less than 2.0% |
| Residual solvents | less than 0.2% |
| Sulfated ash | 4.0–5.0% |

Example of Pharmaceutical Preparations

For the purposes of the present invention the ganglioside $GM_1$, preferably a pharmaceutically acceptable salt thereof, especially the sodium salt, is prepared as a pharmaceutical composition in admixture with one or more pharmaceutically acceptable excipients, carriers or diluents. The ganglioside $GM_1$ can be utilized as a drug in pharmaceutical preparations administered to humans or animals intramuscularly, subcutaneously or intradermally, by intravenous injection or infusion. The preparations can be solutions of the compound or a lyophilized powder of the compound in association with one or more pharmaceutically acceptable carriers or diluents, and contained in buffered media at a suitable pH and isotonic with physiological fluids. The dosage administered will depend upon the desired effect and upon the desired administration route.

The following, although not limitative of the invention, are specific exemplary preparations containing the ganglioside $GM_1$.

Example 1

One vial (or ampoule) is composed as follows:

| | |
|---|---|
| Sodium salt of monosialotetra-hexosylganglioside $GM_1$ | 20.0 mg. |
| Dibasic sodium phosphate.$12H_2O$ | 6.0 mg. |
| Monobasic sodium phosphate.$2H_2O$ | 0.5 mg. |
| Sodium chloride | 16.0 mg. |
| Water for injection, q.s. ad | 2.0 ml. |

Example 2

One vial (or ampoule) is composed as follows:

| | |
|---|---|
| Sodium salt of monosialotetra-hexosylganglioside $GM_1$ | 40.0 mg. |
| Dibasic sodium phosphate.$12H_2O$ | 6.0 mg. |
| Monobasic sodium phosphate.$2H_2O$ | 0.5 mg. |
| Sodium chloride | 16.0 mg. |
| Water for injection, q.s. ad | 2.0 ml. |

Example 3

One vial (or ampoule) is composed as follows:

| | |
|---|---|
| Sodium salt of monosialotetra-hexosylganglioside $GM_1$ | 5.0 mg. |
| Dibasic sodium phosphate.$12H_2O$ | 6.0 mg. |
| Monobasic sodium phosphate.$2H_2O$ | 0.5 mg. |
| Sodium chloride | 16.0 mg. |
| Water for injection, q.s. ad | 2.0 ml. |

Example 4

One vial (or ampoule) is composed as follows:

| | |
|---|---|
| Sodium salt of monosialotetra-hexosylganglioside $GM_1$ | 100.0 mg. |
| Dibasic sodium phosphate.$12H_2O$ | 6.0 mg. |
| Monobasic sodium phosphate.$2H_2O$ | 0.5 mg. |
| Sodium chloride | 16.0 mg. |
| Water for injection, q.s. ad | 2.0 ml. |

Example 5

One vial (or ampoule) is composed as follows:

| | |
|---|---|
| Sodium salt of monosialotetra-hexosylganglioside $GM_1$ | 100.0 mg. |
| Dibasic sodium phosphate.$12H_2O$ | 15.0 mg. |

-continued

| | |
|---|---|
| Monobasic sodium phosphate.2H$_2$O | 1.25 mg. |
| Sodium chloride | 40.0 mg. |
| Water for injection, q.s. ad | 5.0 mg. |

Example 6

One vial (or ampoule) is composed as follows:

| | |
|---|---|
| Sodium salt of monosialotetra-hexosylganglioside GM$_1$ | 300.0 mg. |
| Dibasic sodium phosphate.12H$_2$O | 15.0 mg. |
| Monobasic sodium phosphate.2H$_2$O | 1.25 mg. |
| Sodium chloride | 40.0 mg. |
| Water for injection, q.s. ad | 5.0 ml. |

Pharmacolocical Study

The current study examined the recovery of neurologic function after spinal-cord injury in humans. The model of spinal-cord injury was chosen to examine neurologic recovery in central nervous system tissue because small changes in the size of parenchymal lesions cause large, quantifiable, clinical changes in motor and sensory function distal to the injury. This study was designed as a pilot study to test whether the neurologic recovery in humans after a spinal-cord injury could be altered by adding monosialbtetrahexo-sylganglioside (GM$_1$) ganglioside beyond the routine medical and surgical care with which these trauma patients are initially treated.

Methods

A prospective, randomized, placebo-controlled, double-blinded spinal cord injury GM$_1$ ganglioside drug trial was completed. Of the 37 patients, 34 patients (23 cervical and 11 thoracic injuries) who were randomly assigned to a treatment group and who followed the test drug protocol and completed the one year follow-up period, 16 patients were included in the GM$_1$ group and 18 were in the placebo group.

These patients were 18 years of age or older and had a spinal cord injury with a major neurologic deficit but no other significant injuries or preexisting illness. The first dose of study drug was administered within 72 hours of the injury and then 17 to 29 additional 5 ml daily injections of 100 mg GM$_1$ or placebo were given. The treatment (100 mg of GM$_1$ sodium salt or placebo) was administered duly by the intravenous route for a total of 18–32 doses, with the first dose taken within 72 hours of the injury.

All patients admitted to the shock trauma center with a spinal cord injury were considered for entry to this study.

The criteria for entry were:
1) consent obtained;
2) no contraindication to the use of GM$_1$;
3) female patients either had to be surgically sterile or postmenopausal;
4) age 18 years or older
5) spinal cord lesion with a major motor deficit in the hands or legs.

The criteria for exclusion were:
1) premorbid major medical illness (i.e. end-stage diabetes, heart disease, etc.);
2) high likelihood of being lost to follow-up;
3) involvement in other experimental drug protocols;
4) presence of significant cauda equina damage.

Treatment Composition

The complete composition of the GM$_1$ ganglioside used in the study (Sygen, Fidia, Abano Terme, Italy) is 100 mg of GM$_1$ sodium salt, 12.7 mM; 1.25 mg of sodium dihydrogen phosphate dihydrate, 1.6 mM; 15.0 mg of disodium hydrogen phosphate dodecahydrate, 8.4 mM; 40.0 mg of sodium chloride, 137.9 nM; and a quantity of water sufficient to yield an isotonic solution with a total volume of 5 ml for injection. The placebo vials were identical in appearance and composition, except that the GM$_1$ was absent. Most of the test drug was administered by injection through an intravenous heparin lock. Some of the first few injections were given by an intravenous catheter, and occasionally, when the heparin lock was nonfunctional, a single direct-puncture intravenous injection was used.

The severity of spinal-cord injury and its subsequent recovery were quantified by serial measurement with both the Frankel scale and the American Spinal Injury Association (ASIA) motor score. Each measurement was made at the time of the first contact in the emergency room, at entry into the study, then twice per week for the first 4 weeks and after 2, 3, 6 and 12 months.

The first clinical scale used, that is the Frankel classification system, is extremely important because it provides a very relevant clinical index of neurological improvement of the patients.

More precisely, the Frankel classification system separates neurologic disability into five ordinal grades, according to the type and completeness of neurologic function remaining below the level of the spinal-cord injury, as follows: grad A, complete neurclogic injury; grade B, only sensation preserved; grade C, nonfunctional motor ability preserved; grade D, functional motor ability preserved; and grade E, normal motor function. The letters designating each grade were used by Frankel in his original description of this scale.

The second clinical scale used, that is the ASIA motor score, provides a quantifiable index of nerve-muscle functionality. More exactly, this scale has a range of 0 (complete quadriplegia) to 100 (normal motor function). Five key muscles in each extremity (the biceps, wrist extensors, triceps, flexor profundus, and hand intrinsics in the upper extremity, and the iliopsoas, quadriceps, tibialis anterior, extensor hallucis longus, and gastrocnemius in the lower extremity) are assessed on a scale for strength from 0 to 5 points in which 0 (absent) denotes total paralysis, 1 (trace) palpable or visible penetration, 2(poor) active movement through a range of motion in which gravity is not involved, 3 (fair) active movement through a range of motion against gravity, 4 (good) active movement through a range of motion against resistance, and 5 normal. The ASIA motor score is the sum of the scores for muscle strength in these 20 motor groups.

Results

The distribution of Frankel grades at entry and follow-up according to region of injury and treatment group is shown in Table 1.

TABLE 1

Placebo
Grade at Follow-up

| Grade at Entry | | A | B | C | D | E | Total |
|---|---|---|---|---|---|---|---|
| A | Cv | 4 | | | | | 4 |
|   | Th | 6 | | | | | 6 |
| B | Cv | | | | 1 | | 1 |
|   | Th | | | | | | |
| C | Cv | | | | 2 | | 2 |
|   | Th | | | | 1 | | 1 |
| D | Cv | | | | 3 | 1 | 4 |
|   | Th | | | | | | |
| E | Cv | | | | | | |
|   | Th | | | | | | |
| Total | Cv | | | | 6 | 1 | 11 |
|       | Th | | | | 1 | | 7 |

GM-1
Grade at Follow-up

| Grade at Entry | | A | B | C | D | E | Total |
|---|---|---|---|---|---|---|---|
| A | Cv | 2 | | 1 | | | 3 |
|   | Th | 2 | | | 1 | | 3 |
| B | Cv | | | 4 | | | 4 |
|   | Th | | | | | | |
| C | Cv | | | 2 | 1 | | 3 |
|   | Th | | | | | 1 | 1 |
| D | Cv | | | | 2 | | 2 |
|   | Th | | | | | | |
| E | Cv | | | | | | |
|   | Th | | | | | | |
| Total | Cv | 2 | | 3 | 7 | | 12 |
|       | Th | 2 | | | 1 | 1 | 4 |

The distribution in each table is subdivided according to the region of injury, cervical (Cv) or thoracic (Th). Patients whose data are shown in the main diagonal (heavily outlined boxes from upper left to lower right) had no change in grade over the one year period. The grades obtained at entry revealed no bias according to either group or anatomical region of injury.

The improvements in these grades after one year revealed the following points:

- the overall number of patients whose scores improved by two or more Frankel grades was larger than historical data would have predicted (23.5 percent, or 8 of 34 patients, in this study as compared with 4.4 percent in historical data.
- the majority of the patients (seven of eight) who had this considerable neurologic recovery were in the $GM_1$ group.
- in the placebo group, the recovery observed was similar to that predicted on the basis of historical data (1 of 18 patients, or 5.6 percent).

The above results demonstrate that the $GM_1$-treated patients improved more than the placebo-treated patients with respect to Frankel grade (P=0.034 by the Cochran-Mantel-Haenszel chi-square test). Furthermore, among 28 patients who had room to improve by two or more Frankel grades, 7 of 14 of the $GM_1$-treated patients improved as compared with 1 of 14 of the placebo-treated patients (50 percent vs. 7.1 percent, P=0.033 by Fisher's exact test, two-tailed).

ASIA Classification

The distribution of improvement in ASIA motor scores from study entry to the end of the one-year follow-up is shown in FIG. 1 for each treatment group. Data are shown for 15 patients treated with GM-1 and 18 patients given placebo. There was a skew toward lower scores for recovery in the placebo group as compared with the GM-1 group. The obtained results show that there were more patients with motor recoveries or more than 20 points in the $GM_1$ group (11 of 16), or 68.8 percent) than in the placebo group (7 of 18, or 38.9 percent). Also, three $GM_1$-treated patients had a greater degree of recovery than any patient assigned to placebo, and there were more patients with no recovery in the placebo group (six patients) than in the $GM_1$ group (one patient).

Table 1 shows the ASIA motor scores at entry, those after the one-year follow-up, and the improvement in mean scores during this period, according to treatment group, for all patients completing the study and for the subgroup of patients with cervical injuries; it also presents the mean, standard deviation, and 95 percent Student's t confidence intervals. There was an imbalance in the mean ASIA motor scores at study entry despite randomization, with greater motor deficit in the $GM_1$ group. The mean ASIA motor score at entry was 25.9 (95 percent confidence interval, 14.3 to 37.5) for the $GM_1$ group and 39.8 (95 percent confidence interval, 29.5 to 50.1) for the placebo group.

TABLE 2

Mean ASIA Motor Scores at Study Entry
and Follow-up, with Improvements in Scores, for
all Patients and the Subgroup of Cervical
Patients, According to Treatment Group.

| Treatment Group | Mean = SD | # in Group | 95% Confidence Interval* |
|---|---|---|---|
| All patients | | | |
| Placebo | | | |
| Entry | 39.8 ± 20.7 | 18 | 29.5–50.1 |
| Follow-up | 61.4 ± 26.5 | 18 | 48.3–74.6 |
| Improvement | 21.6 ± 23.0 | 18 | 10.2–33.1 |
| $GM_1$ | | | |
| Entry | 25.9 ± 21.8 | 16 | 14.3–37.5 |
| Follow-up | 62.8 ± 26.8 | 16 | 48.5–77.1 |
| Improvement | 36.9 ± 28.2 | 16 | 21.9–51.9 |
| Difference in improvement between groups | | | |
| Unadjusted | 15.3 ± 25.6 | 34 | −2.6–32.2 |
| Adjusted | 11.5 ± 5.6+ | 34 | 0.2–22.9§ |

*Intervals shown are 95 percent Student's t confidence intervals.
+Denotes the adjusted mean = SE on the basis of an analysis of covanance with the base-line ASIA motor score as the covanate.
§Denotes the 95 percent Student's t confidence interval for the adjusted mean = (adjusted mean) = (standard error) $t_{0.975,30}$, where $t_{0.975,30}$ = 97.5 percent percentile of Student's t distribution with 30 degrees of freedom.

The $GM_1$-treated patients had a mean motor recovery of 36.9 points (95 percent confidence interval, 21.9 to 51.9) from their ASIA motor score at entry to the score after one year, whereas for the placebo-treated patients the mean recovery was 21.6 points (95 percent confidence interval, 10.2 to 33.1).

Also shown in Table 2 are the difference between treatment groups in improvement in ASIA motor score (mean, 15.3; 95 percent confidence interval, −2.6 to 32.2) and the difference in improvement as calculated after adjustment for the difference in base-line values by an analysis of covariance in which the base-line score was used as a covariate (mean, 11.5; 95 percent confidence interval, 0.2 to 22.9). The adjusted difference in the improvement of motor recovery between the two groups was significant for drug effect (P=0.043 by analysis of covariance with the base-line ASIA motor score as the covariate).

Furthermore, to better analyze the $GM_1$ effect on muscular functionality, the 20 individual muscle groups in each patient were subdivided into three categories at entry: those initially paralyzed (a motor score of 0), those initially paretic (a motor score of 1 through 4), and those functioning normally (a motor score of 5). At the end of the study, an imbalance was noted in the pattern of recovery between treatment groups when the proportion of muscle groups paralyzed at entry (those with a motor score of 0) that regained useful-to-normal function (a motor scope of 3 to 5) after one year was compared with the proportion that remained paralyzed. In the $GM_1$ group, 30.9 percent of the paralyzed muscle groups (64 of 207) remained paralyzed, and 51.7 percent (107 of 207) recovered to regain useful-to-normal motor function; in the placebo group, 65.5 percent (127 of 194) remained paralyzed, and 25.3 percent (49 of 194) regained useful-to-normal motor function.

Since the muscles do not recover independently (typically when improvement occurs, several muscle groups improve) a post hoc analysis was developed, however, to address muscle-group improvement on a per-patient basis that conformed with the requirement for independence of statistical tests. The number of patients in each treatment group who had at least one paralyzed muscle group at entry that improved to a motor score of 3 or more at the one-year follow-up was compared with the number of patients who had no muscle group paralyzed at entry for which there was that degree of improvement. This analysis revealed a significant drug effect (13 of 16, or 81.3 percent, in the $GM_1$ group and 8 of 18 or 44.4 percent, in the placebo group; P=0.039 by Fisher's exact test, two-tailed) and demonstrates the drug effect, is due to the regaining of useful function by paralyzed muscles rather than to paretic muscles improving strength.

Discussion of Test Results

The above reported results are very indicative of a remarkable neuro beneficial efficacy of $GM_1$ in the treatment of spinal cord injury. It is extremely important to remove the indication obtained from the evaluation of the patients according to the Frankel scale.

In fact, the improvement of patients by two or three Frankel grades in this study represents a dramatic increase in neurologic function, with the majority of these patients changing from paralyzed to ambulatory status. Furthermore, the marked improvement in the recovery of paralyzed motor groups (ASIA scale), along with the similar recovery of the paretic muscles in the two treatment groups, indicates that the observed effect of $GM_1$ occurs by the conversion of motor groups initially paralyzed into those with useful motor function after one year.

Combination Therapy

Because the first injection of $GM_1$ occurred a mean of 48 hours after the injury and was continued in a sub-acute/chronic phase, the drug effect is presumably by a different mechanism than has been proposed with other drug administration protocols (such as several steroid or steroid-related compounds, thyroid-releasing hormone, naloxone, and most notably methylprednisolone administered within 8 hours after the injury) that are designed for maximal benefit in the hyperacute phase of injury. However, the combination of $GM_1$ administered according to this study protocol and methylprednisolone or other potentially active drug given in the hyperacute phase has the potential of being more than additive if such drugs allow the initial survival of injured neurons and then $GM_1$ permits the maintenance of survival. There is also the potential that $GM_1$ administered in the hyperacute phase could have additional benefits because $GM_1$ is efficacious in decreasing the death of some type of neurons in some experimental in vitro conditions. Furthermore, in view of the herein results demonstrating long-term $GM_1$ effects, it may be expected that $GM_1$ has the potential to act synergistically also with eventual drugs presumed to be efficacious in the chronic stage of spinal cord injury. The present invention, therefore, includes either the treatment with $GM_1$ per se (i.e. alone) (in the hyperacute-acute-subacute and chronic phase) or the combination of methylprednisolone (or other potentially active drugs) and $GM_1$. These combinations (or associations) include either the concurrent treatment (for example, in the hyperacute phase, that is initially within the first eight hours after the lesion) and/or the sequential treatment (for example, after the initial hyperacute administration of methylprednisolone, or other drugs, followed by the administration of $GM_1$, preferably within 24–72 hours after the lesion, and prolonged in the sub-acute/chronic phase).

Methylprednisolone is usually administered at a dosage of 100 to 20,000 mg per dose, preferably 250 to 10,000 mg per dose and $GM_1$ is administered at a dosage of 100 to 500 mg per dose, preferably at 100–200 mg per dose. Both of the pharmacological treatments can be administered by various routes, preferably by intravenous and/or intramuscular routes.

Methylprednisolone can be administered per se and is commercially available from various sources. Alternatively, methylprednisol one can be administered in the form of an ester with hyaluronic acid (HY). Such esters of hyaluronic acid with pharmacologically active alcohols, such as methylprednisolone, are described together with their method of preparation in U.S. Pat. No. 4,851,52 1. That is, the compound can be in the form of a "total" ester wherein all of the carboxylic groups of the hyaluronic acid are esterified with methylprednisolone. Alternatively, the compound can be in the form of a "partial" ester wherein only a portion of the carboxylic groups of the hyaluronic acid are esterified with methylprednisolone, and the remaining groups are free acid groups or salified, such as with sodium.

For example, for the preparation of a partial ester of methylprednisolone with hyaluronic acid (i.e. wherein 25% of the HY carboxylic groups are esterified and 75% are salified with Na), the following procedure can be utilized.

6.2 g of HY tetrabutylammonium salt with a molecular weight of 105,000 corresponding to 10 m.Eq. of a monomeric unit are solubilized in 310 ml of dimethylsulfoxide at 25° C. of methylprednisolone are added and the resulting solution is kept for 24 hours at 30° C.

A solution containing 100 ml of water and 5 g of sodium chloride is added and the resulting mixture is slowly poured into 2,000 ml of acetone under constant agitation. A precipitate is formed which filtered and washed three times with 100 ml of acetone/water 5:1 and three times with acetone and finally vacuum dried for eight hours at 30° C.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30° C. 4.5 g of the partial methylprednisolone ester compound are obtained.

The HY-methylprednisolone ester can then be administered in the form of a pharmaceutical preparation in combination with pharmaceutically acceptable diluents or excipients and may be employed for oral, rectal, parenteral, subcutaneous, local or intradermal use. In addition, the ester can be prepared in the form of microcapsules, produced by spray-drying and suspended in acceptable carriers or diluents.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for treatment of spinal cord injury in a patient, which comprises (a) administration to said patient of a therapeutically effective amount of methylprednisolone within 8 hours after the occurrence of said injury, and (b) after completion of the administration of methylprednisolone but within about 24–72 hours after said injury, initial administration to said patient of a therapeutically effective amount of ganglioside $GM_1$, wherein the therapeutically effective amounts are those which would permit survival of injured neurons.

2. The method according to claim 1, wherein said $GM_1$ is initially administered within about 24–48 hours after the occurrence of the spinal-cord injury.

3. The method according to claim 1, wherein said $GM_1$ is administered in an amount of about 100 to 500 mg per dose.

4. The method according to claim 1, wherein said dose is 100 to 500 mg per day.

5. The method according to claim 1, wherein said dose is 100 mg per day.

6. The method according to claim 1, wherein said methylprednisolone is administered in the form of an ester with hyaluronic acid.

* * * * *